US009034436B1

(12) United States Patent  
Finkenstadt et al.

(10) Patent No.: US 9,034,436 B1  
(45) Date of Patent: May 19, 2015

(54) ANTI-CORROSION COATING UTILIZING BACTERIAL PRECIPITATED EXOPOLYSACCHARIDES

(75) Inventors: Victoria L. Finkenstadt, Peoria, IL (US); Gregory L. Cote, Edwards, IL (US); Julious L. Willett, Morton, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 694 days.

(21) Appl. No.: 13/242,050

(22) Filed: Sep. 23, 2011

Related U.S. Application Data

(60) Provisional application No. 61/388,093, filed on Sep. 30, 2010.

(51) Int. Cl.
    *B05D 5/00* (2006.01)
    *C23F 11/173* (2006.01)
    *C09D 105/02* (2006.01)

(52) U.S. Cl.
    CPC ............... *B05D 5/00* (2013.01); *C09D 105/02* (2013.01); *B05D 2202/10* (2013.01); *C23F 11/173* (2013.01)

(58) Field of Classification Search
    None
    See application file for complete search history.

(56) References Cited

U.S. PATENT DOCUMENTS

| 2,295,204 A * | 9/1942 | Dockray .......................... 134/28 |
| 2,734,828 A * | 2/1956 | Toulmin ...................... 106/205.8 |
| 2,756,156 A * | 7/1956 | Hiler ........................... 106/14.27 |
| 5,789,209 A * | 8/1998 | Leathers et al. ............... 435/101 |
| 6,031,058 A * | 2/2000 | McIntosh et al. .............. 526/171 |
| 2006/0226515 A1 * | 10/2006 | Yamada et al. ............... 257/630 |

FOREIGN PATENT DOCUMENTS

WO    03/008618 A2    1/2003

OTHER PUBLICATIONS

ARS Culture Collection (NRRL) Database lookup for NRRL B-1501, accessed at http://nrrl.ncaur.usda.gov /cgi-bin/usda/prokaryote/report.html?nrrlcodes=B-1501 on Apr. 9, 2014.*
Jeanes, Allene, et al., "Characterization and Classification of Dextrans from Ninety-Six Strains of Bacteria", Dextrans from Ninety-Six Strains of Bacteria, vol. 76, pp. 5041-5052, Oct. 20, 1954.

* cited by examiner

*Primary Examiner* — Timothy Meeks
*Assistant Examiner* — Michael P Rodriguez
(74) *Attorney, Agent, or Firm* — John Fado; Albert Y. Tsui; Lesley Shaw

(57) ABSTRACT

Disclosed is a method for inhibiting corrosion on corrosion-sensitive metal with a bacterial exopolysaccharide. Specifically, exopolysaccharides precipitated from NRRL bacterial strains B-1254, B-1355, B-1498, and B-1500 coated on low carbon steel alloy confers anti-corrosion coating to corrosion sensitive metals. Preferably with the coating, the corrosion rate for coated metal is less than 0.4 milli-inch per year.

11 Claims, 6 Drawing Sheets

Before

After

Flash corrosion of low-carbon steel without exopolysaccharide coating

Before          After

Flash corrosion of low-carbon steel coated with exopolysaccharide precipitated fromB-1498 fraction-L[S]

Before After

Flash corrosion of low-carbon steel without exopolysaccharide coating

Before After

Flash corrosion of low-carbon steel coated with native, mixed-fraction exopolysaccharide precipitated from B-1355

ANTI-CORROSION COATING UTILIZING BACTERIAL PRECIPITATED EXOPOLYSACCHARIDES

CROSS-REFERENCE TO RELATED APPLICATION

This present application claims priority under 35 U.S.C. §119(e) to U.S. Provisional Ser. No. 61/388,093, which was filed on Sep. 30, 2010, the disclosure of which is hereby incorporated by reference.

FIELD OF THE INVENTION

Disclosed is a method for inhibiting corrosion on corrosion-sensitive metal with a bacterial exopolysaccharide. Specifically, exopolysaccharides precipitated from NRRL bacterial strains B-1254, B-1355, B-1498, and B-1500 coated on low carbon steel alloy confers anti-corrosion coating to corrosion sensitive metals. Preferably with the coating, the corrosion rate for coated metal is less than 0.4 milli-inch per year.

BACKGROUND OF INVENTION

The corrosion of metal degrades iron-based tools and structures presents a challenging problem to industries worldwide. When metals come in contact with different environments such as air, water, chemical products, and pollutants, they begin to degrade as a result of the metal interacting with its environment. For example, rusting is the loss of electrons from metals reacting with water and oxygen. This type of electrochemical corrosion causes severe damage to industrial equipment, materials, and buildings.

Current corrosion control measures include non-electrochemical means by galvanizing metal with an inexpensive metallic element. Typically, the galvanization process coats steel with zinc. Additionally, there are electrochemical means of protecting metal from corrosion via a cathodic protection wherein the metal to be protected acts as a cathode and is in electrochemical contact with another more corrosive metal acting as an anode. However, these measures have the disadvantage of being costly measure for controlling corrosion. The adoption of preventive measures that reduce or eliminate corrosion is financially costly and time consuming. The National Institute of Standards and Technology (NIST) estimated in 1996 that the cost of corrosion for the United States is over $300 billion. Given high cost of corrosion control there is a need to explore other corrosion control methods.

Other corrosion protection control means include applying a protective paint or epoxy coating to form a physical barrier between the metal surface from oxidizing with oxygen. The measure of applying a protective coating on metals has the advantage that the coating can be applied post-manufacturing of the metal. However, using such a protective coating has the drawback of necessitating constant maintenance through re-application inasmuch as a rupture in the coating allows for localized corrosion to occur under the protective coat and ultimately disputes the protective coating. Ideally, a protective coating would have self-healing properties and would not require re-application or minimize re-application.

Microbial populations have been observed to both increase as well as decrease the rate of metal corrosion. As detailed in Jayaramna et al., 1997, *Journal of Industrial Microbiology & Biotechnology*, 18, 396-401, cultures of bacterial species of *Pseudomonas* sp., *Bacillus* sp., and *Hafnia alvei*, have induced corrosion of mild steel. On the other hand, cultures of aerobic bacteria species *Pseudomonans* S9 and *Serratia marscens* EF190 have been shown to confer a 10-fold corrosion inhibition of SIS 1146 steel. See Pedersen et al., 1989, Biofouling 1:313-322. Additionally, it has been reported that bacteria species *Pseudomonas fragi* and *Escherichia coli* DH5α(pKMY319) conferred corrosion protection of mild steel in a LB medium. See Jayaraman, et al., 1997, *App Microbiol Biotechnol*, 47:62-68. In these cases, the metal was submerged in an aqueous medium inoculated by a bacterial species. The bacteria colonized the metal substrate and excreted a heterogeneous exopolysaccharide adhering to metal surfaces facilitated by the functional groups of the exopolymer substance.

Various bacteria, such as *Leuconostoc* sp., produce exopolysaccharides into their surroundings. As disclosed in WO 03/008618, an α-1,6 glucan produced by *Lactobacillus* strain LMG P-20349 during the growth phase conferred anti-corrosion properties to plain carbon steel sheets that were exposed to slightly corrosive medium of 0.1M $LiClO_4$. The treated sheet with the *Lactobacillus* strain produced exopolysaccharide left a thin black layer, whereas the control and sheets covered with an exopolysaccharide from *Lactobacillus sake* displayed corrosion and localized corrosion respectively. Given the differences in anticorrosion properties of exopolysaccharides produced by different bacteria strains, there is a need in the art to determine as to which exopolysaccharides provide corrosion inhibition properties.

BRIEF SUMMARY OF THE INVENTION

Disclose herein is a method for inhibiting corrosion on corrosion-sensitive metal with a bacterial exopolysaccharide, the method comprising culturing a bacterial strain wherein the bacterial strain is selected from strains NRRL B-1254, NRRL B-1355, NRRL B-1498, or NRRL B-1500, precipitating a substantially pure exopolysaccharide fraction from said culture, applying the substantially pure exopolysaccharide to corrosion-sensitive metal. In one embodiment of the invention corrosion-sensitive metal having an exopolysaccharide applied to said metal has a corrosive rate of less than 0.4 milli-inch per year.

In an embodiment, the exopolysaccharide is precipitated from a cell-free culture fluid. In another embodiment of the invention, the exopolysaccharide prevents corrosion in a pure salt oxidization environment. In various embodiments of the invention, the exopolysaccharide fraction is a mixed, native fraction precipitated from strain NRRL B-1254, a L-fraction precipitated from strain NRRL B-1498, or a L[S]-fraction precipitated from strain NRRL B-1254.

In one embodiment of the invention, the exopolysaccharide fraction is applied via spray coating, while in another embodiment the exopolysaccharide fraction is applied via cast films. In another embodiment of the invention, the exopolysaccharide is applied to the corrosion-sensitive metal at a minimum thickness of approximately 50 nm. In yet another embodiment of the invention, the corrosion-sensitive metal is a low carbon steel alloy.

Disclosed herein is a method for inhibiting corrosion on corrosion-sensitive metal with a bacterial derived exopolysaccharide, the method comprising coating steel with an aqueous solution of substantially pure exopolysaccharide, wherein the exopolysaccharide is precipitated from a *Leuconostoc* species culture, wherein the culture is selected from the group consisting of NRRL B-1254, NRRL B-1355, NRRL B-1498, and NRRL B 1501. In one embodiment of the invention, the exopolysaccharide is precipitated from strain NRRL B-1254. In another embodiment of the invention, the exopolysaccharide fraction is precipitated from strain NRRL B-1498. In another embodiment of the invention, the exopolysaccharide is precipitated from strain NRRL B-1355. In another embodiment of the invention, the exopolysaccharide is precipitated from strain NRRL B-1500. In yet another embodiment of the invention, the exopolysaccharide is applied to low carbon steel alloy.

Also disclosed herein is a steel metal alloy comprising a substrate with an exterior surface; and a protective coating positioned on said exterior surface that reduces corrosion of said exterior surface; wherein said coating comprises a exopolysaccharide coating precipitated from a bacterial culture selected from the group consisting of NRRL B-1254, NRRL B-1355, NRRL B-1498, and NRRL B-1500. In one embodiment of the invention, the metal alloy is a low carbon steel alloy.

DETAILED DESCRIPTION OF THE INVENTION

Definitions

Figure 1A:
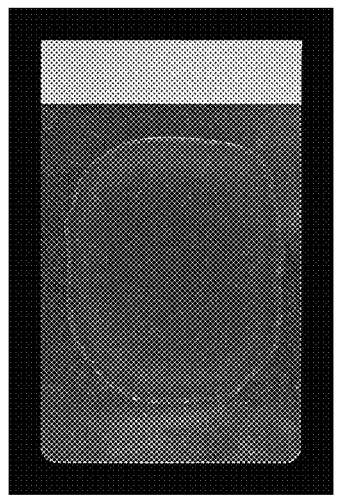
FIG. 1A depicts exopolysaccharide coating derived from B-1498 cast on a SAE 1010 steel panel for flash corrosion purposes. The depiction shows the panel coated with a dime sized L-fraction exopolysaccharide and allowing the exopolysaccharide to dry with a subsequent depiction of the area after subjecting the coated area to electrochemical impedance measurement.
Figure 1A:
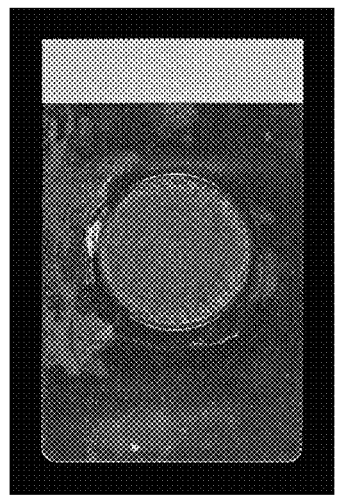

As used in the specification and claims, the singular form "a", "an" and "the" include plural references unless the context clearly dictates otherwise. For example, the term "a cell" includes a plurality of cells, including mixtures thereof.

As used in the specification and claims, the term "biofilm" refers to high molecular weight matrix of polymeric substance embedded with an aggregate of microorganism that produced the polymeric substance. An example of polymeric substance produced is exopolysaccharides. Exemplar microorganisms that produce exopolysaccharides include, but are not limited to bacterial species such as *Leuconostoc mesenteroides, Leuconostoc citreum, Lactobacillus satsumensis, Desulfovibrio* sp., *Thiobacillus* sp., as well as autotrophic algae sources. In the case of *Leuconostoc* species, various exopolysaccharides are secreted in culture requiring the exopolysaccharides to be extracted. An example of extracting exopolysaccharides from culture includes an ethanol extraction method, as detailed infra.

As used in the specification and claims, the term "substantially pure exopolysacharide" refers to an exopolysaccharide having a high degree of purity relative to that which is extracted from culture or extracted from a microorganism cell outer surface. One of skill in the art will readily recognize that any exopolysaccharide, even after purification, may contain a "contaminant" to a greater or lesser degree. Accordingly, although the purified chemical compounds have been "purified," absolute purity may not necessarily be obtained without significant sacrifice of yield.

Different exopolysaccharide fractions are precipitated from bacterial strains depending on the percentage of alcohol in which the exopolysaccharide precipitates from solution. Exopolysaccharide fractions precipitated from identified bacterial strains are identified by the exopolysaccharide solubility in water-alcohol mixtures. In general, the designation "L-fraction" is recognized as a less soluble fraction exopolysaccharide fraction precipitated from a bacterial strain, whereas a "S-fraction" designates a more soluble fraction. A fraction having a "N" designation is a native unfractionated mixture of "S" and "L" fractions.

As used herein, "L-fraction" refers to exopolysaccharides that precipitate from supercentrifugation in a concentration range that is specific to the strain of bacteria in question. For NRRL B-1355, fraction L is that fraction which precipitates at an ethanol concentration of 36-37% whereas fraction S precipitates at an ethanol concentration of 39-41% when performed under the conditions defined by C. A. Witham, C. A., et al., 1955, Archives of Biochemistry and Biophysics 59:61-75. The L-fractions and S-fractions from strain B-1498 precipitate in essentially the same ethanol range as the L- and S-fractions from B-1355. In the instance of NRRL B-1254, fraction L was originally reported to precipitate at an ethanol concentration of approximately 35-36%, whereas fraction S precipitated at 36-37% ethanol. It should be pointed out that these alcohol percentages may vary according to temperature, dextran concentration, and other variables, but fraction L is always less soluble in alcohol-water mixtures relative to fraction S.

Particular to fractions obtained from B-1254, Seymour, R. D., et al., 1979, Carbohydrate Research 68:123-140, proposed switching the designations for B-1254 fractions, based on structural information, so that fraction L became fraction S[L] and fraction S became fraction L[S]. To avoid ambiguity, as used herein for B-1254 derived fractions, the nomenclature disclosed in Seymour et al. will be used.

As defined herein, corrosion rate of milli-inch per year was calculated via the formula:

$$C.R. = 0.13 \frac{(Icorr)(EW)}{D}$$

wherein Icorr is the corrosion current, EW is the equivalent weight of species, and D is density.

Purified exopolysaccharides produced from bacteria were dispersed in nanopure water and cast onto SAE 1018 steel. Tested exopolysaccharides along with their culture source are listed infra in Table 1 for flash corrosion. Electrochemical Impedance Measurements are listed in Table 2.

As used herein, bacterial strains NRRL B-1254, B-1355, B-1498, B-1254, B-1500, B-1213, B-1203, B-1208, B-1254, B-1417, B-1290, B-1212, B-742, B-1422, B-1207, B-1384, B-1395, B-1382, B-1390, B-1216, B-1527, B-1211, B-1499, B-1145, B-1202, B-1127, B-1525, and B-1205 denote bacterial strains found in the general collection of the ARS Open Culture Collection at 1815 N. University Street, Peoria, Ill.

*Leuconostoc* spp. strains were grown as previously described and the cell-free culture fluids were used to produce polysaccharide from sucrose. Specifically, the exopolysaccharides were extracted by incubating a buffered solution (pH 5.1-5.6) solution of 0.3M sucrose solution with alternansucrase with the culture. After a period of 1-5 days at room temperature, upon the mixture become viscous and visually opalescent, absolute ethanol was added at room temperature with continual stirring until the polysaccharide precipitated.

TABLE 1

| Exopolysaccharide and Fraction | Source Description | Monomers | Linkages Backbone, Branch* |
|---|---|---|---|
| B-1498, Fraction-L | *Leuconostoc mesenteroides* NRRL B-1498, fraction L, dextran | α-D-glucose | α(1→6), α(1→3) |
| B-1498, Fraction-S | *Leuconostoc mesenteroides* NRRL B-1498, fraction S, alternan | α-D-glucose | α(1→3) (1→6) (alternating) |
| B-1498, Fraction-N | *Leuconostoc mesenteroides* NRRL B-1498, mixed native fraction | α-D-glucose | α(1→6) and α(1→3) |
| B-1355, Fraction-L | *Leuconostoc mesenteroides* NRRL B-1355, fraction L, dextran | α-D-glucose | α(1→6), α(1→3) |
| B-1355, Fraction-S, | *Leuconostoc mesenteroides* NRRL B-1355, fraction S, alternan | α-D-glucose | α(1→3) (1→6) (alternating) |
| B-1355, Fraction-N | *Leuconostoc mesenteroides* NRRL B-1355, mixed native fraction | α-D-glucose | α(1→3) and (1→6) |

*Branch point is defined as di-substituted sugar

While the exopolysaccharides described above are isolated from growth cultures, the exopolysaccharides can also be prepared enzymatically from cell-free culture fluid. Techniques to derive exopolysaccharides from cell-free culture is described in A. Jeanes, Dextrans, pp. 118-132, in R. L. Whistler, Ed., Methods in Carbohydrate Chemistry, V.5, 1965, Academic Press, NY, and incorporated herein by reference.

Application of exopolysaccharides to metal can be achieved through a myriad of ways. One method is to cast the purified exopolysaccharides onto the metal. Typically this involves rolling an aqueous solution of an exopolysaccharide on a metal substrate.

Another application of exopolysaccharides to a metal substrate can be achieved through spraying the exopolysaccharide via liquid spraying techniques.

It is contemplated that that use of the exopolysaccharide as described herein would be compatible with many existing technologies for thin films deposition, including physical and chemical vapor deposition and sputtering on a substrate. Collectively, these techniques are usable to produce thin films of many materials for a wide variety of applications. Application of the disclosed exopolysaccharide to a substrate as a protective coating includes but is not limited to spray applications, sputter deposition, dipping applications, casting applications, rolling applications, pasting applications, and laminate applications.

The water soluble solutions of polysaccharides were spray painted on SAE 1010 low carbon cold rolled steel panels (Type R35, Q-Panel Lab Products, Cleveland Ohio) via a Badger Air Brush set. The exopolysaccharide coating was applied to the metal substrate by twice passing the air brush across the metal substrate at a distance of approximately 12 inches. Upon application of the coating, the sample was allowed to dry overnight at room temperature of 20° C. at approximately 30% relative humidity. Steel panels were sonicated in hexane and rinsed with 50-50 ethanol/methanol solution prior to metal coating application. Measurement of sprayed films was determined by atomic force microscopy via Nanoscope IV by Veeco, Inc.

Electrochemical Impedance Spectroscopy

Applied exopolysaccharide coatings were evaluated via electrochemical impedance spectroscopy. For all electrochemical impedance measures, metal substrates were sprayed painted with a exopolysaccharide as detailed above. The electrochemical impedance measurements evaluated the ability of a circuit to resist flow of electrical current with a dependency on frequency. The AC current and voltage signal through the resistor (corrosion solution) do not need to be in phase with each other.

Electrochemical measurements for precipitated exopolysaccharides were coated on low carbon metal and were evaluated using a PARSTAT 2273 Advanced Potentiostat (Princeton Applied Research, Oak Ridge, Tenn.) having a 3 electrode cell. The test cell was a Gamry PTC1 Paint Test Cell (Gamry Instrument, Warminster, Pa.) equipped with a three electrode system. The working electrode was a plate of R-35 stainless steel on top of which a 50 ml open glass tube was sealed with a rubber gasket. The electrolyte solution was poured into the newly created container from the top. The graphite counter and saturated calomel electrodes were also inserted through the stopper-engaged top. The working electrode active test area was approximately 14.0 cm$^2$. The electrochemical impedance spectroscopy (EIS) scanned ±10 mV, AC about the open circuit (corrosion) potential of the cell with frequencies between 100 kHz and 10 mHz. 10 points per decade were recorded and averaged. The cell was brought to a steady corrosion state for 24 hours in the same solution the experiments were conducted in, before recording the spectra. All tests were performed in either 5% weight/volume NaCl solution or 0.5 M sulfuric acid.

Analysis was performed using an electrochemistry software including modules specifically designed for AC and DC corrosion measurements and analysis of Tafel, Nyquist, and Bode plots (Princeton Applied Research, Oak Ridge, Tenn.). Pore resistance is a measurement of the penetration of an electrolyte through the film and its subsequent reaction at the metal surface. Pore resistance, as measured from the low frequency domains of electrochemical impedance, was calculated and the relative effectiveness of the coatings was determined.

The following examples are intended to further illustrate the invention, without any intent for the invention to be limited to the specific embodiments described therein. All patents and publications cited herein are incorporated by reference.

Not to be bound by any theory of explanation on why a particular exopolysaccharide coatings confer corrosion protection, it is believed that the adherence of the polysaccharide is facilitated at least in part by the interaction of metal ions and the functional groups of the polysaccharide. Specifically, it is believed that the a polysaccharides having the functional hydroxyl groups cross linking with each hydroxyl groups confer better binding of the polysaccharides with the metal alloy. Generally, it is believed that the cross-linking alters the redox potential of Fe(II) or Fe(III) by reducing the amount of electron acceptors at the metal-polysaccharide interface by binding Fe(II) and Fe(III). This a based on the visual confirmation of the presence of black iron (FeII) oxide and orange rust iron (FeIII) and that hydroxyl groups chelate with positively charged iron which slows the equilibrium-favored conversion of FeII to FeIII.

EXAMPLE 1

Flash Corrosion Exopolysaccharides Coating Low-Carbon Steel Alloys

Exopolysaccharide samples (0.5 g) were dissolved in approximately 20 ml of nanopure water and cast on SAE 1010 steel. Thickness of the exopolysaccharide was measured by dried coating was measured by using a MiniTest 2100 (ElektroPhysik, Germany). As detailed supra, the coating was allowed to air dry followed by subjecting the spray coated to electrochemical impedance measurements. FIG. 1A depicts L-fraction coating from B-1498 conferring minimal flash corrosion.

Figure 1B:
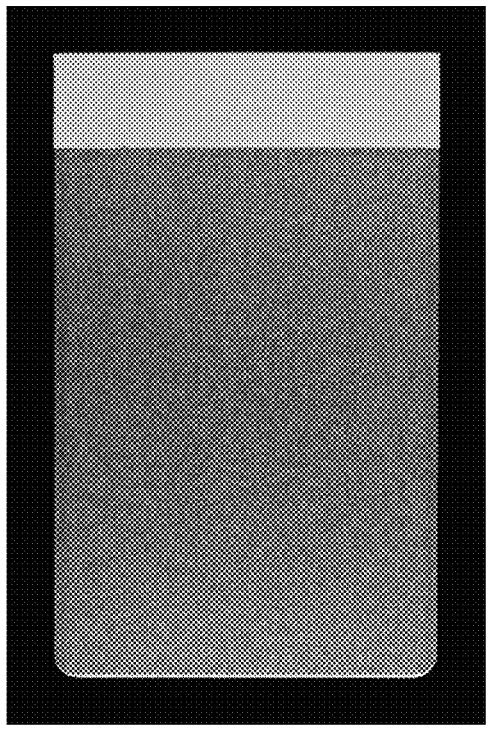
FIG. 1B depicts a SAE 1010 steel panel without any exopolysaccharide coatings. A subsequent depiction shows an electrochemical impedance measurement of a dime sized area.
Figure 1B:
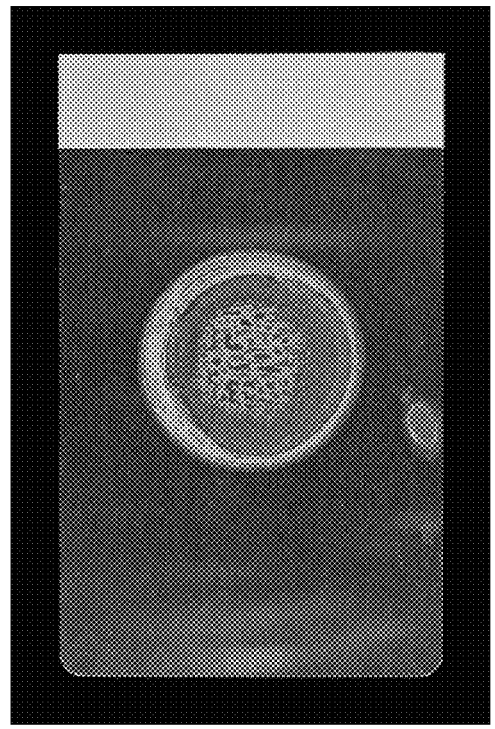

FIG. 1B show the flash corrosion of on the SAE steel without any exopolysaccharide coating applied on the metal.

Figure 1C:
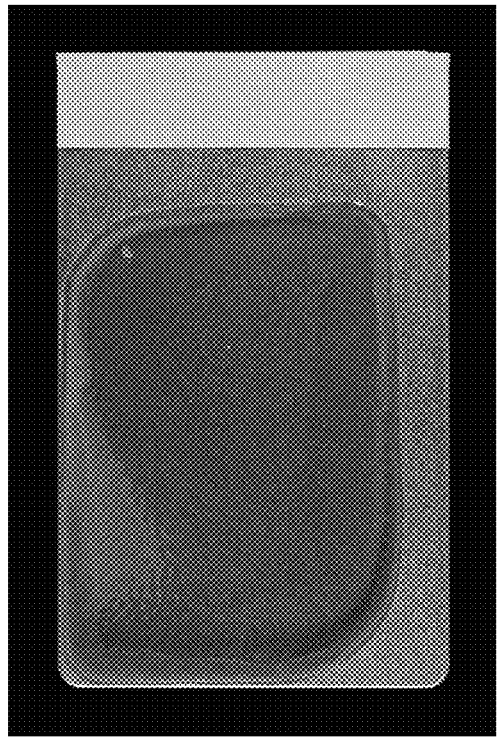
FIG. 1C depicts exopolysaccharide coating derived from B-1355 cast on a SAE 1010 steel panel for flash corrosion purposes. The depiction shows the panel coated with a dime sized native, mixed-fraction exopolysaccharide and allowing the exopolysaccharide to dry with a subsequent depiction of the area after subjecting the coated area to electrochemical impedance measurement.
Figure 1C:
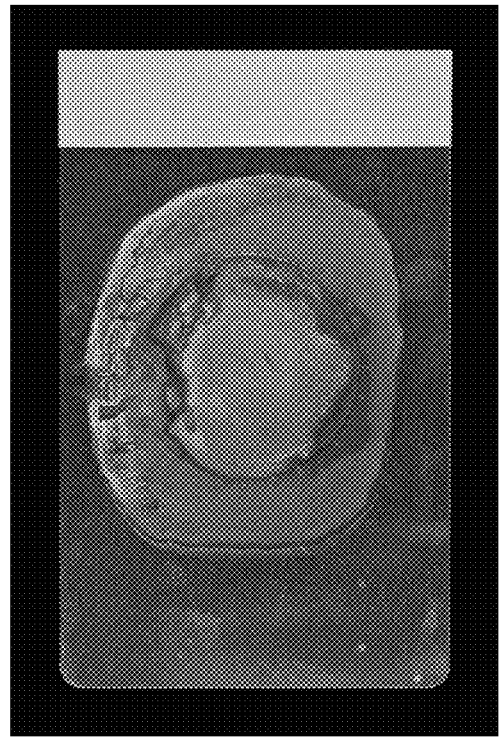
Figure 2:
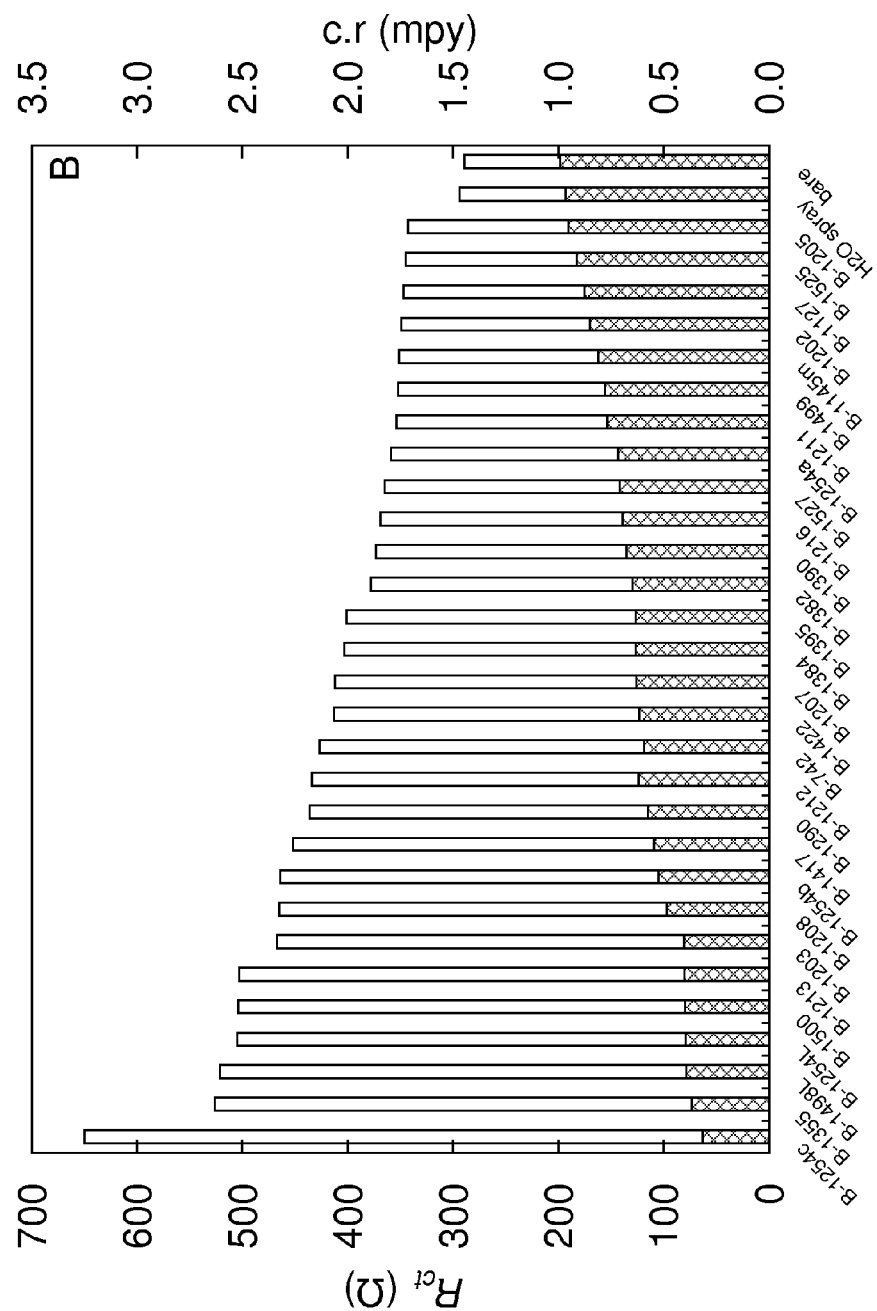
FIG. 2 is a graph of polarized resistance (solid bar graph) and corrosion rate (hatched bar graph) for a plurality of exopolysaccharides precipitated from NRRL B-1254, B-1355, B-1498, B-1500, B-1213, B-1203, B-1208, B-1417, B-1290, B-1212, B-742, B-1422, B-1207, B-1384, B-1395, B-1382, B-1390, B-1216, B-1527, B-1211, B-1499, B-1202, B-1127, B-1525, B-1205, bare metal, and water spray on coated on SAE 1010 steel.
Figure 3:
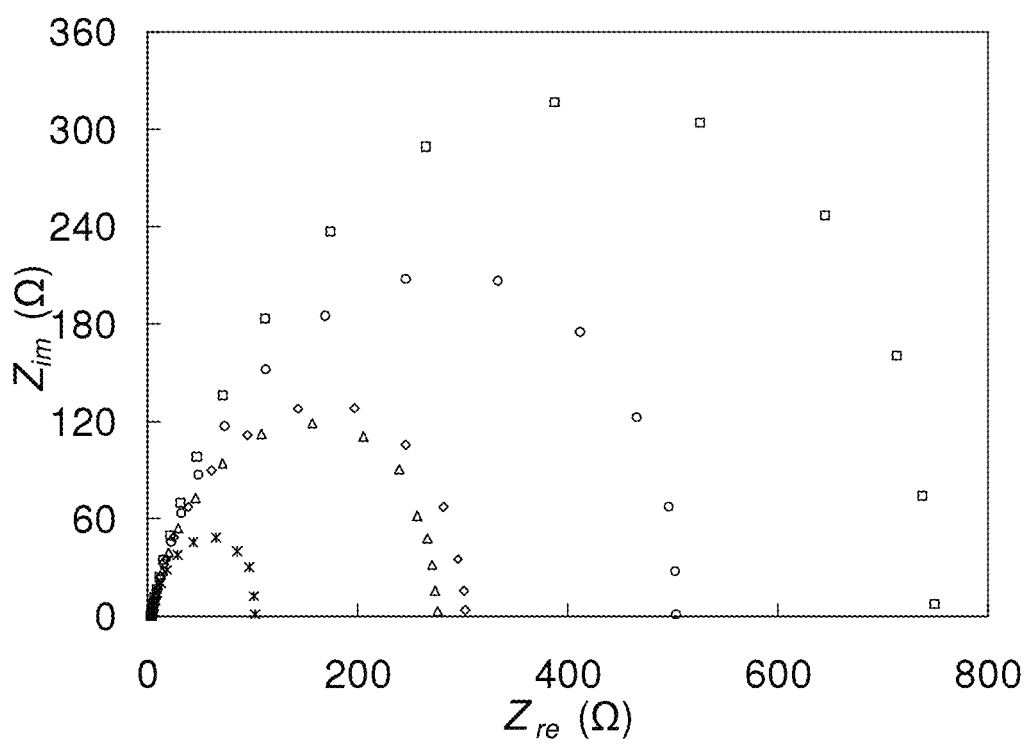
FIG. 3 is a Nyquist plot of an electrochemical impedance response of 30 to 50 nanometers thick coating on SAE 1010 steel of a L[S]-fraction exopolysaccharide precipitated from NRRL B-1254 (Δ), a L-fraction exopolysaccharide precipitated from NRRL B-1498 (◇), a fraction exopolysaccharide precipitated from NRRL B-1355 (○), a native, mixed-fraction exopolysaccharide precipitated from NRRL B-1254 (□), and uncoated metal as represented by an asterisk (*).
Figure 4:
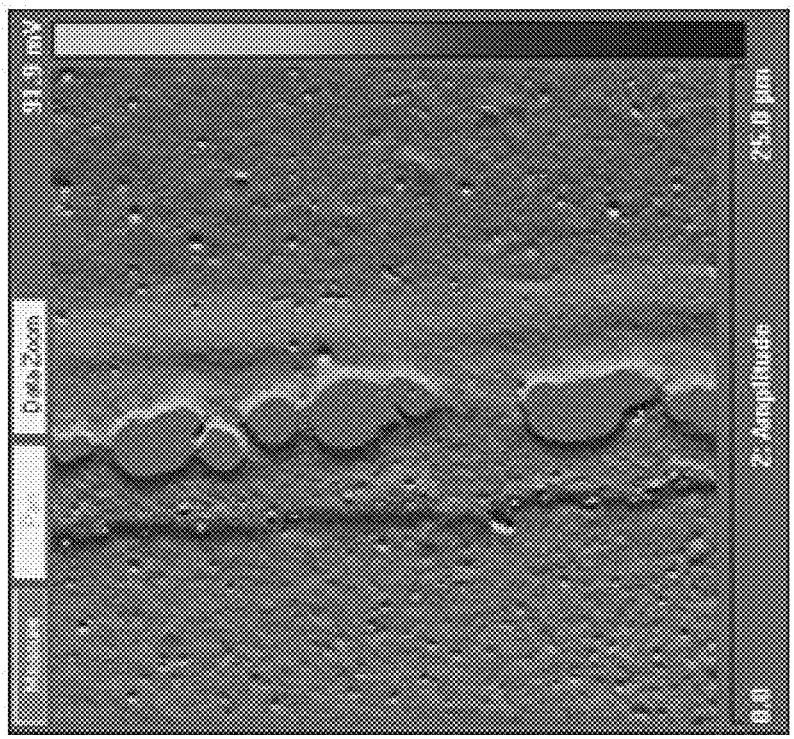
FIG. 4 depicts an atomic force microscopy image of a native, mixed-fraction exopolysaccharide precipitated from NRRL B-1355 and having a scratch followed by the self-healing property of the exopolysaccharide after 15 second immersion in water.
Figure 4:
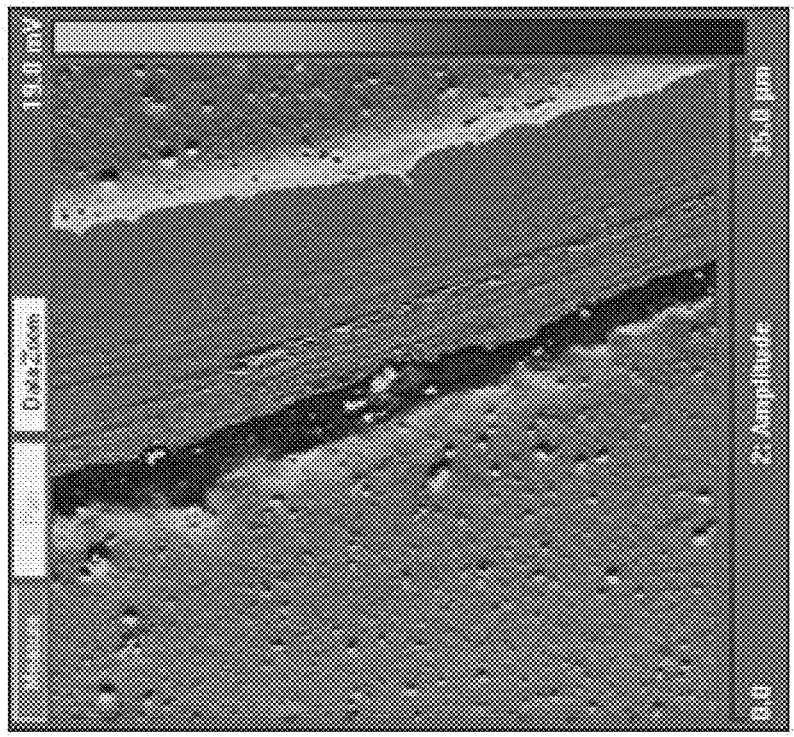

FIG. 1C shows a typical reaction of SAE 1010 steel after coating with several different exopolysaccharide systems. The formation of flash corrosion occurred within a few minutes after casting.

However, in the case of coating the low carbon steel plate with an exopolysaccharide precipitated from B-1355, flash corrosion was visible and developed after developed during drying of the biofilm.

EXAMPLE 2

Electrochemical Analysis of B-1254, Mixed Native Fraction

Exopolysaccharides derived from B-1498, mixed native fraction was sprayed on SAE 1010 steel panel as an aqueous solution as detailed supra. The thickness of the sprayed on film was determined by atomic force microscopy. In this particular case, the biofilm sprayed on the steel panel had a thickness between 50 nm to 500 nm. As detailed in Table 2, precipitated from B-1254, was subject to electrochemical analysis.

TABLE 2

| Film | Rct (Ω) | Cd (mF) | Etafel (−V) | icorr (μA) | c.r (mpy) |
|---|---|---|---|---|---|
| B-1254[c] | 650 | 23.11 | 0.669 | 10.26 | 0.315 |
| B-1355 | 526 | 22.26 | 0.719 | 11.12 | 0.366 |
| B-1498L | 521 | 22.19 | 0.75 | 11.56 | 0.393 |
| B-1254L | 505 | 21.02 | 0.763 | 11.85 | 0.395 |
| B-1500 | 504 | 20.11 | 0.768 | 12.01 | 0.399 |
| B-1213 | 503 | 19.46 | 0.761 | 12.2 | 0.402 |
| B-1203 | 467 | 18.66 | 0.767 | 12.24 | 0.403 |
| B-1208 | 465 | 18.36 | 0.772 | 14.76 | 0.486 |
| B-1254[b] | 464 | 18.34 | 0.775 | 15.9 | 0.523 |
| B-1417 | 452 | 18.08 | 0.781 | 16.95 | 0.545 |
| B-1290 | 436 | 17.69 | 0.784 | 17.49 | 0.576 |
| B-1212 | 434 | 17.29 | 0.789 | 18.83 | 0.619 |
| B-742 | 427 | 17.18 | 0.792 | 18.01 | 0.593 |
| B-1422 | 413 | 17.11 | 0.795 | 18.97 | 0.615 |
| B-1207 | 412 | 16.45 | 0.798 | 19.13 | 0.629 |
| B-1384 | 403 | 16.36 | 0.799 | 22.49 | 0.631 |
| B-1395 | 401 | 16.22 | 0.81 | 22.86 | 0.632 |
| B-1382 | 378 | 16.03 | 0.812 | 23.46 | 0.649 |
| B-1390 | 373 | 15.36 | 0.819 | 24.01 | 0.678 |
| B-1216 | 369 | 15.2 | 0.821 | 24.15 | 0.694 |
| B-1527 | 365 | 15.18 | 0.828 | 24.89 | 0.708 |
| B-1254[a] | 359 | 14.6 | 0.831 | 25.08 | 0.715 |
| B-1211 | 354 | 14.57 | 0.835 | 25.67 | 0.768 |
| B-1499 | 352 | 14.01 | 0.832 | 25.98 | 0.779 |
| B-1145m | 351 | 13.06 | 0.841 | 26.07 | 0.812 |
| B-1202 | 349 | 12.59 | 0.849 | 26.59 | 0.851 |
| B-1127 | 347 | 12.12 | 0.856 | 26.84 | 0.875 |
| B-1525 | 345 | 12.06 | 0.859 | 27.68 | 0.912 |
| B-1205 | 343 | 11.77 | 0.868 | 28.57 | 0.951 |
| H2O spray | 294 | 10.59 | 0.871 | 29.32 | 0.965 |
| bare | 289 | 9.114 | 0.872 | 30.14 | 0.992 |

Letters a, b, and c refer to different preparations of B-1254 native dextran, each containing different amounts of fractions S and L.

Letters a, b, and c refer to different preparations of B-1254 native dextran, each containing different amounts of fractions S[ L ] and L[ S ].

EXAMPLE 3

Electrochemical Analysis of B-1355

Exopolysaccharides derived from B-1355, was sprayed on SAE 1010 steel panel as an aqueous solution as detailed supra. The thickness of the sprayed on film was determined by atomic force microscopy. In this particular case, the biofilm sprayed on the steel panel had a thickness of between 50 nm to 500 nm. As detailed in Table 2, the exopolysaccharide precipitated from B-1355 was subjected to electrochemical analysis.

EXAMPLE 4

Electrochemical Analysis of B-1498, Fraction-L

Exopolysaccharides derived from B-1498, fraction-L was sprayed on SAE 1010 steel panel as an aqueous solution as detailed supra. The thickness of the sprayed on film was determined by atomic force microscopy. In this particular case, the biofilm sprayed on the steel panel had a thickness between 50 nm to 500 nm. As detailed in Table 2, fraction-L precipitated from B-1498 was subjected to electrochemical analysis.

EXAMPLE 5

Electrochemical Analysis of B-1254, Fraction-L[ S ]

Exopolysaccharides derived from B-1254, fraction-L[ S ] was sprayed on SAE 1010 steel panel as an aqueous solution as detailed supra. The thickness of the sprayed on film was determined by atomic force microscopy. In this particular case, the biofilm sprayed on the steel panel had a thickness between 50 nm to 500 nm. As detailed in Table 2, fraction-L[S] precipitated from B-1254 was subjected to electrochemical analysis.

EXAMPLE 6

Electrochemical Analysis of B-1500 B-1501

Exopolysaccharides derived from B-1500 was sprayed on SAE 1010 steel panel as an aqueous solution as detailed supra. The thickness of the sprayed on film was determined by atomic force microscopy. In this particular case, the biofilm sprayed on the steel panel had a thickness between 50 nm to 500 nm. As detailed in Table 2, the exopolysaccharide precipitated from B-1500 was subjected to electrochemical analysis.

While the invention has been described with reference to details of the illustrated embodiment, these details are not intended to limit the scope of the invention as defined in the appended claims.

The embodiment of the invention in which exclusive property or privilege is claimed is defined as follows:

1. A method for inhibiting corrosion on corrosion-sensitive metal with a bacterial exopolysaccharide, the method comprising:
    culturing a NRRL B-1254 bacterial strain,
    precipitating a substantially pure exopolysaccharide fraction from said culture,
    applying the substantially pure exopolysaccharide fraction to corrosion-sensitive metal, wherein the metal corrosion rate of the corrosion-sensitive metal having the exopolysaccharide applied thereto is inhibited.

2. The method of claim 1 wherein an iron corrosion rate of the corrosion-sensitive metal having the exopolysaccharide applied thereto is less than 0.4 milli-inches per year.

3. The method of claim 1 wherein the exopolysaccharide is precipitated from a cell-free culture fluid.

4. The method of claim 1 wherein the exopolysaccharide fraction is a L[S] fraction precipitated from strain NRRL B-1254.

5. The method of claim 1, wherein the corrosion-sensitive metal is a low carbon steel alloy.

6. The method of claim 1, wherein the exopolysaccharide prevents corrosion in a pure salt oxidization environment.

7. The method of claim 1 wherein the exopolysaccharide fraction is applied via spray coating.

8. The method of claim 7 wherein the exopolysaccharide fraction is applied to the corrosion-sensitive metal at a minimum thickness of approximately 50 nm.

9. The method of claim 1 wherein the exopolysaccharide fraction is applied via cast films.

10. A method for inhibiting corrosion on corrosion-sensitive metal with a bacterial exopolysaccharide, the method comprising:
    coating steel with an aqueous solution of substantially pure exopolysaccharide, wherein the exopolysaccharide is precipitated from a NRRL B-1254 bacterial culture.

11. The method of claim 10 wherein the steel is a low carbon steel alloy.

* * * * *